(12) United States Patent
Ouchi

(10) Patent No.: US 8,995,613 B2
(45) Date of Patent: Mar. 31, 2015

(54) X-RAY IMAGING APPARATUS

(75) Inventor: Chidane Ouchi, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 300 days.

(21) Appl. No.: 13/518,233

(22) PCT Filed: Feb. 14, 2011

(86) PCT No.: PCT/JP2011/053585
§ 371 (c)(1),
(2), (4) Date: Jun. 21, 2012

(87) PCT Pub. No.: WO2011/105306
PCT Pub. Date: Sep. 1, 2011

(65) Prior Publication Data
US 2012/0263274 A1    Oct. 18, 2012

(30) Foreign Application Priority Data
Feb. 23, 2010   (JP) ................. 2010-036909

(51) Int. Cl.
*A61B 6/00* (2006.01)
*G21K 1/06* (2006.01)
*G01N 23/04* (2006.01)
*G01N 23/20* (2006.01)

(52) U.S. Cl.
CPC ........... *G21K 1/06* (2013.01); *G01N 23/046* (2013.01); *G01N 23/20075* (2013.01); *A61B 6/484* (2013.01); *G01N 2223/064* (2013.01); *G21K 2207/005* (2013.01); *G01N 2223/419* (2013.01)
USPC ........................................ 378/62

(58) Field of Classification Search
USPC ............................. 378/36, 62, 82
See application file for complete search history.

(56) References Cited

U.S. PATENT DOCUMENTS

| | | | |
|---|---|---|---|
| 2010/0054415 A1* | 3/2010 | Olivo et al. | 378/85 |
| 2011/0206184 A1* | 8/2011 | Mukaide et al. | 378/62 |
| 2012/0236988 A1 | 9/2012 | Den et al. | |
| 2012/0281217 A1 | 11/2012 | Ouchi et al. | |

FOREIGN PATENT DOCUMENTS

| | | |
|---|---|---|
| GB | 2441578 | 3/2008 |
| WO | WO 2008/029107 | 3/2008 |
| WO | WO 2010/147125 | 12/2010 |

OTHER PUBLICATIONS

Y. Nesterets et al., "Phase Contrast Imaging Using a Scanning-Double-Grating Configuration", *Optics Express*, vol. 16, No. 8, pp. 5849-5867 (2008).

* cited by examiner

*Primary Examiner* — Glen Kao
(74) *Attorney, Agent, or Firm* — Fitzpatrick, Cella, Harper & Scinto

(57) ABSTRACT

An X-ray imaging apparatus which takes an image of an object to be detected, comprises: a first grating to form a periodic bright-dark pattern by a Talbot effect, based on an X-ray from an X-ray source; a second grating, disposed at a position where the bright-dark pattern is formed, to block a part of the bright-dark pattern; a detector to detect an X-ray intensity distribution of the X-ray which passed through the second grating; and a calculator to calculate phase information of the X-ray based on the detected X-ray intensity distribution, wherein the second grating includes a first region having a first blocking pattern and a second region having a second blocking pattern, and a direction in which the first blocking pattern blocks a bright section of the bright-dark pattern is different from a direction in which the second blocking pattern blocks the bright section of the bright-dark pattern.

9 Claims, 10 Drawing Sheets

X-RAY IMAGING APPARATUS

TECHNICAL FIELD

The present invention relates to an X-ray imaging apparatus.

BACKGROUND ART

An X-ray has high material transparency, and can achieve imaging with high spatial resolution. For these reasons, the X-ray is used for a nondestructive inspection of an object as industrial utilization, X-raying as medical utilization, and the like.

That is, by the X-ray in the above utilization, a contrast image is formed by using a difference of absorption in a case where the X-ray transmits through an object or a living body, due to constituent elements and density differences of the object or the living body. It should be noted that such a process is called an X-ray absorption contrast method.

However, since an X-ray absorption capability of a light element is very small, it is difficult by the X-ray absorption contrast method to take an image of living soft tissue which consists of carbon, hydrogen, oxygen and the like being constituent elements of the living body, or a soft material.

On the other hand, in order to provide a method which can clearly take an image of even tissue consisting of light elements, a research for a phase contrast method using a phase difference of X-rays has been performed since 1990's.

Among numerous phase contrast methods developed, a method capable of obtaining an image by a single X-ray imaging is desirable for somatoscopy, and particularly for medical somatoscopy. For example, a method described in PTL 1 and a method described in NPL 1 have been proposed.

More specifically, in the method described in PTL 1, an X-ray is divided by periodically arranged slits so that the divided X-ray corresponds to a pixel of a detector. Further, an X-ray shielding mask is arranged at the edge of the pixel of the detector, and slight deviation in an X-ray direction which arises when the X-ray transmits through an object to be detected is detected as an output change of the pixel, whereby a phase image is obtained from a first imaging.

Further, in a Scanning Double Grating method (hereinafter, called an SDG method) in NPL 1, imaging is performed while a diffraction grating which forms a self-image and an absorption grating which is disposed at the position of the self-image are simultaneously scanned in the same direction. Thus, an inclination of wavefront of an X-ray is detected as an intensity change through a single imaging, whereby a phase image is obtained.

CITATION LISTS

Patent Literature

PTL 1: International Application Publication WO2008/029107

Non Patent Literature

NPL 1: SDG ("Phase Contrast Imaging using Scanning-Double-Grating Configuration", Y. Nesterets and S. Wilkins, April 2008/Vol. 16, No. 8/OPTICS EXPRESS)

SUMMARY OF INVENTION

Technical Problem

In each of the methods described in PTL 1 and NPL 1, in a case where absorption of the X-rays existing in the object to be detected is non-uniformly distributed, the non-uniformly distributed absorption becomes an error factor, whereby quality of the obtained phase image deteriorates.

In consideration of such a problem, the present invention aims to provide an X-ray imaging apparatus which can reduce an influence of a transmissivity distribution of the X-ray in the object to be detected even in the case where there is the non-uniformly distributed absorption in the object to be detected, and thus take the phase image having exceptional quality.

Solution to Problem

In one aspect of the present invention, an X-ray imaging apparatus, which takes an image of an object to be detected, is characterized by comprising; an X-ray source, a first grating configured to form a periodic bright-dark pattern by a Talbot effect, on the basis of an X-ray from the X-ray source, a second grating, disposed at a position where the bright-dark pattern is formed, configured to block a part of the bright-dark pattern, a detector configured to detect an X-ray intensity distribution of the X-ray which passed through the second grating; and a calculator configured to calculate phase information of the X-ray on the basis of the X-ray intensity distribution detected by the detector, wherein the second grating includes a first region in which a first blocking pattern has been formed and a second region in which a second blocking pattern has been formed, and a direction in which the first blocking pattern blocks a bright section of the bright-dark pattern and a direction in which the second blocking pattern blocks the bright section of the bright-dark pattern are different from each other. Other aspects of the present invention will be clarified in the following exemplary embodiments of the present invention.

Further features of the present invention will become apparent from the following description of exemplary embodiments with reference to the attached drawings.

BRIEF DESCRIPTION OF DRAWINGS

FIG. 1 is a block diagram for describing an X-ray imaging apparatus in an example 1 of the present invention.

FIG. 2A is a diagram for describing a first grating in an example 2 of the present invention. FIG. 2B is a diagram illustrating a bright-dark pattern in the example 2.

FIG. 3A is a diagram for describing a second grating in the example 2. FIG. 3B is a diagram for describing an overlapping state of a bright section of the bright-dark pattern and a blocking section in the example 2.

FIG. 4A is another diagram for describing the second grating in the example 2. FIG. 4B is another diagram for describing an overlapping state of a bright section of the bright-dark pattern and a blocking section in the example 2.

FIG. 5A is a diagram for describing a first grating in an example 3. FIG. 5B is a diagram for describing an overlapping state of a bright section of the bright-dark pattern and a blocking section in the example 3.

FIG. 6A is a diagram for describing a second grating in the example 3. FIG. 6B is another diagram for describing an overlapping state of a bright section of the bright-dark pattern and a blocking section in the example 3.

FIG. 7A is a diagram for describing a first grating in an example 4. FIG. 7B is a diagram illustrating a bright-dark pattern in the example 4.

FIG. 8A is a diagram for describing a second grating in the example 4. FIG. 8B is a diagram for describing an overlapping state of a bright section of the bright-dark pattern and a blocking section in the example 4.

FIG. 9A is another diagram for describing the second grating in the example 4. FIG. 9B is another diagram for describing an overlapping state of a bright section of the bright-dark pattern and a blocking section in the example 4.

FIG. 10A is a diagram for describing a first grating in an example 5. FIG. 10B is a diagram illustrating a bright-dark pattern in the example 5.

DESCRIPTION OF EMBODIMENTS

Figure 1:
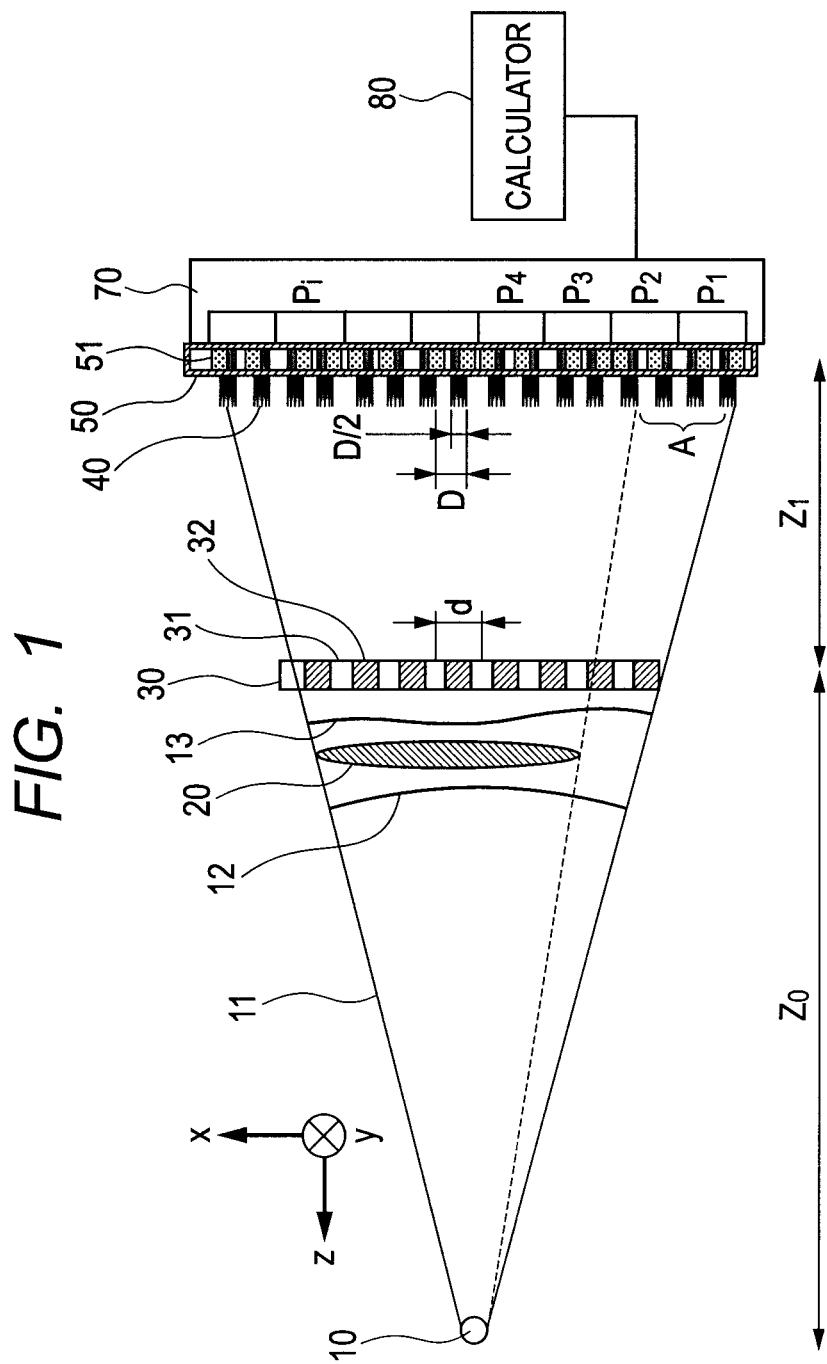
[FIG. 1]

Hereinafter, a constructive example of an X-ray imaging apparatus which takes a phase image by a Talbot effect using an X-ray, according to an exemplary embodiment of the present invention will be described.

The X-ray imaging apparatus according to the present embodiment comprises:

an X-ray source which radiates an X-ray;

a first grating which is disposed at the position to which the X-ray is incident from the X-ray source and forms a periodic bright-dark pattern by a Talbot effect using the transmitting X-ray;

a second grating which is disposed at the position where the bright-dark pattern is formed by the first grating, and blocks a part of the bright-dark pattern; and an X-ray intensity detector which detects X-ray intensity information based on an X-ray intensity distribution of the X-ray transmitted through an object to be detected disposed between the first grating and the second grating or between the first grating and the X-ray source.

Thus, the X-ray imaging apparatus obtains, by a calculator, phase information of the X-ray from the X-ray intensity information detected by the X-ray intensity detector.

In the X-ray imaging apparatus thus constructed, the X-ray necessary for measurement is radiated by the X-ray source toward the object to be detected.

The object to be detected is disposed between the first grating and the second grating or between the first grating and the X-ray source, and the periodic bright-dark pattern is formed by the Talbot effect using the X-ray transmitting through the first grating.

The first grating is constructed by an absorption member on which openings are periodically arranged. Concretely, the first grating is constructed by, for example, a phase grating composed of an X-ray transmitting member of which the thickness periodically changes, or a slit which has periodically arranged openings.

The second grating is disposed so as to block a part of the bright section of the bright-dark pattern formed by the first grating.

That is, in order to block a part of the bright-dark pattern, the second grating has a first region in which a first blocking pattern is formed and a second region in which a second blocking pattern is formed, as the regions on which the blocking patterns extending mutually opposite directions respectively are formed in regard to the periodicity direction of the bright-dark pattern.

Here, concretely, the respective blocking patterns block, for example, right and left halves, upper and lower halves, or oblique-45° halves of the pattern.

Further, with respect to the bright-dark patterns which are incident to the same pixel of the X-ray intensity detector, the blocking directions thereof are set to be the same.

Therefore, if the bright-dark pattern moves in the direction perpendicular to the blocking direction, an amount of received light of the corresponding pixel changes.

If an inclination of a wavefront changes according to transmission of the X-ray through the object to be detected, an X-ray direction changes, and the bright-dark pattern on the second grating thus moves.

Therefore, an inclination of a transmitted wavefront (hereinafter, called a differential wavefront) of the object to be detected can be obtained based on an output change of the relevant pixel. However, since the object to be detected generally includes a uniform transmissivity distribution caused by absorption of the X-ray, the amount of received light of the relevant pixel also changes by the uniform transmissivity distribution.

In the present embodiment, in order to reduce an influence by the transmissivity distribution in the object to be detected, the second gratings respectively provided on the adjacent pixels are set so that the blocking directions thereof are mutually opposite to each other.

In the output changes of these two pixels, the changes caused by the absorption occur in phase. However, since the changes caused by the movement of the bright-dark pattern occur in reversed phases, the influence of the transmissivity distribution can be reduced by separating these changes, whereby the accurate differential wavefront can be obtained.

In the calculator of the X-ray imaging apparatus according to the present embodiment, calculation is performed as follows.

Namely, a ratio of a difference between the outputs of a pair of the pixels respectively blocked in the opposite directions and a sum of these outputs is obtained, and the obtained ratio is multiplied by a proportionality constant determined a distance between the first grating and the second grating and a period of the first grating, whereby the inclination of the wavefront at a relevant portion is obtained.

Then, the above-described calculation is performed to the overall effective region of the X-ray intensity detector, whereby the differential wavefront is calculated.

Also, the calculator can calculate the transmitted wavefront of the object to be detected by integrating the differential wavefronts concerning the perpendicular two directions.

EXAMPLES

Hereinafter, examples of the present invention will be described.

Example 1

As an example 1, a construction of the X-ray imaging apparatus to which the present invention is applied will be described with reference to FIG. 1.

This drawing illustrates an X-ray source 10 which radiates an X-ray, an X-ray 11 which is radiated by the X-ray source 10, and an object 20 to be detected which is to be measured by the X-ray imaging apparatus. Further, this drawing illustrates a first grating 30 which is used to form a periodic bright-dark pattern by the transmitting X-ray, a bright section 40 of the bright-dark pattern formed by the first grating 30, and a second grating 50 which blocks a part of the bright section 40 of the bright-dark pattern.

Furthermore, this drawing illustrates an X-ray intensity detector 70 which takes and detects an X-ray image received, and pixels $P_i$ (i=1, 2, 3, . . . ) of the X-ray intensity detector 70.

Furthermore, this drawing illustrates a calculator 80 which calculates a differential wavefront and a transmitted wavefront from the image which has been taken by the X-ray intensity detector 70.

In the above construction, the X-ray 11 radiated from the X-ray source 10 passes through the object 20 to be detected and the first grating 30, and then reaches the second grating 50.

The first grating 30 is manufactured by silicone of which X-ray transmissivity is large and which has excellent workability.

A phase modulation grating of a phase difference $\pi$ or $\pi/2$ (hereinafter, called a one-dimensional $\pi$ phase grating or a one-dimensional $\pi/2$ phase grating) that a portion where a phase of the transmitting X-ray is relatively different by $\pi$ or $\pi/2$ is one-dimensionally and periodically arranged is formed by periodically changing the thickness of the silicone.

That is, the thickness of a hatched portion 32 is made different from the thickness of a non-hatched portion 31 so that a transmission phase of the hatched portion 32 is different from a transmission phase of the non-hatched portion 31 by $\pi$ or $\pi/2$.

The X-ray transmitting section and the blocking section are periodically arranged on the second grating 50, and a blocking section 51 is manufactured by gold which is a member for satisfactorily blocking the X-ray.

The second grating 50 is disposed at a position where the Talbot effect by the first grating 30 arises based on the X-ray radiated from the X-ray source 10 (hereinafter, called a Talbot position).

That is, if it is assumed that a distance between the X-ray source and the first grating is $Z_0$ and a distance between the first grating 30 and the second grating 50 is $Z_1$, the second grating is disposed so as to satisfy the following expression (1).

In the expression (1), $\lambda$ indicates a wavelength of the X-ray, d indicates a grating period of the first grating 30, n indicates a natural number, and N indicates a real number which is expressed as $n/4-1/8$ in case of the one-dimensional $\pi$ phase grating and as $n-1/2$ in case of the one-dimensional $\pi/2$ phase grating.

$$1/Z_0 + 1/Z_1 = 1/N \times \lambda/d^2 \quad (1)$$

The periodic bright-dark pattern is generated by the Talbot effect on the second grating 50.

The blocking section 51 of the second grating 50 is disposed at the position of blocking a part of the bright section 40 of the bright-dark pattern.

When passing through the object 20 to be detected, a wavefront 12 of the X-ray 11 deforms according to its refractive-index distribution, whereby a transmitted wavefront 13 is obtained.

The bright section 40 moves in proportion to an inclination change of the corresponding section of the transmitted wavefront 13. An amount of light of the X-ray which reaches the X-ray intensity detector 70 through the second grating 50 changes according to an amount of the movement.

The size of the pixel is set to be equal to an integral multiple of the period of the bright-dark pattern so as to make the number of the bright sections 40 for light reception of each pixel constant for all the pixels.

If the intensity of the bright section 40 radiated to the second grating 50 is identical, an inclination of the transmitted wavefront 13 can be calculated because it is proportional to a change amount of the amount of received light.

However, since the intensity of the bright section 40 of the bright-dark pattern depends on X-ray transmissivity of the object 20 to be detected, an amount of movement of the bright section 40 cannot be calculated only by the change of the amount of received light of each pixel if the X-ray transmissivity is uneven.

For this reason, in this example, in order to be able to calculate the amount of movement of the bright section 40 even if the X-ray transmissivity is uneven, the direction in which the blocking section 51 of the second grating 50 blocks the bright section 40 is set to be identical on the same pixel of the X-ray intensity detector 70. On the other hand, the direction in which the blocking section 51 of the second grating 50 blocks the bright section 40 on one pixel is set to be opposite to the direction in which the blocking section 51 of the second grating 50 blocks the bright section 40 on the adjacent pixel.

That is, the blocking by the first blocking pattern of the first region on the pixel $P_{2n-1}$ aims at the left half, while the blocking by the second blocking pattern of the second region on the pixel $P_{2n}$ aims at the right half.

Here, it is assumed that n=1, 2, 3, . . . . Therefore, for example, the amount of received light in a case where the bright section 40 moves in the x direction being the direction perpendicular to the gratings (lines) of the first grating 30 due to an inclination of the wavefront increases in the pixels $P_1$ and $P_3$, but decreases in the pixels $P_2$ and $P_4$. Further, since the size of each pixel is generally small, the magnitude of intensity of the bright section 40 in one pixel can be considered to be approximately the same as that in its adjacent pixel, and the magnitude of movement of the bright section 40 in one pixel can be considered to be approximately the same as that in its adjacent pixel. Therefore, a normalized intensity change which is obtained by dividing a difference between the outputs of the adjacent pixels by a sum of these outputs does not depend on the intensity of the bright sections 40, but is proportional only to an average value of the amounts of movements of the bright sections 40 of these two pixels.

That is, the normalized intensity change $A_1$ at an intermediate position $P_1'$ of the pixels $P_1$ and $P_2$ is defined by the following expression (2), and the normalized intensity change $A_2$ at the intermediate position $P_2'$ of the pixels $P_2$ and $P_3$ is defined by the following expression (3). Hereinafter, if the normalized intensity change $A_i$ at the intermediate position $P_i'$ of the pixels $P_i$ and $P_{i+1}$ is likewise defined by the following expression (4), in general, the normalized intensity change $A_i$ (i=1, 2, 3, . . .) is proportional only to the change of the bright section 40 in the x direction without being influenced by the transmissivity distribution of the object 20 to be detected.

$$A_1 = -(I_2 - I_1)/(I_2 + I_1) \quad (2)$$

$$A_2 = (I_3 - I_2)/(I_3 + I_2) \quad (3)$$

Generally, the following expression is established.

$$A_i = (-1)^i \times (I_{i+1} - I_i)/(I_{i+1} + I_i) \quad (4)$$

Here, it should be noted that $I_1$ is the output of the pixel $P_1$, $I_2$ is the output of the pixel $P_2$, and $I_i$ is the output of the pixel $P_i$. Further, if it is assumed that the period of the bright-dark pattern is D, the width of the bright section 40 is D/2. Further, since the half of the bright section is blocked, the width of the X-ray received by the pixel is D/4.

If it is assumed that an average of the amount of the movements of the bright sections 40 in the pixels $P_i$ and $P_{i+1}$ is $\Delta L_i$, as each of $I_i$ and $I_{i+1}$ is proportional to an area of the not-blocked portion of the brightness section, $I_i$ is proportional to $D/4 + \Delta L_i$ if i is an odd number, while $I_i$ is proportional to $D/4 - \Delta L_i$ if i is an even number.

Consequently, the following expression (5) is obtained from the expression (4).

$$A_i = -\{(D/4 - \Delta L_i) - (D/4 + \Delta L_i)\}/\{(D/4 - \Delta L_i) + (D/4 + \Delta L_i)\}$$
$$= 4\Delta L_i/D \text{ (}i\text{: odd number)}$$

$$A_i = \{(D/4 + \Delta L_i) - (D/4 - \Delta L_i)\}/\{(D/4 + \Delta L_i) + (D/4 - \Delta L_i)\}$$
$$= 4\Delta L_i/D \text{ (}i\text{: even number)}$$

(5)

Here, the period D of the bright-dark pattern is expressed by the following expressions (6) and (7) using the grating period d of the first grating 30, the distance $Z_0$ between the X-ray source and the first grating, and the distance $Z_1$ between the first grating 30 and the second grating 50. That is, in the case where the one-dimensional π phase grating is used, the period D is expressed by the following expression (6).

$$D=(1+Z_1/Z_0) \times d/2 \quad (6)$$

Further, in the case where the one-dimensional π/2 phase grating is used, the period D is expressed by the following expression (7).

$$D=(1+Z_1/Z_0) \times d \quad (7)$$

The inclination $Wx_i$ of the wavefront in the periodic direction (x direction in FIG. 1) perpendicular to the grating direction of the first grating 30 at the point corresponding to the point $P_i$ on the transmitted wavefront 13 satisfies the relation of the following expression (8).

$$Wx_i = \Delta L_i/Z_1 \quad (8)$$

Therefore, in the case where the one-dimensional π phase grating is used, the following expression (9) is obtained from the expressions (8), (5) and (6).

$$Wx_i = A_i/8 \times (1/Z_0 + 1/Z_1) \times d \quad (9)$$

Likewise, in the case where the one-dimensional π/2 phase grating is used, the following expression (10) is obtained from the expressions (8), (5) and (7).

$$Wx_i = A_i/4 \times (1/Z_0 + 1/Z_1) \times d \quad (10)$$

Furthermore, in the case where the one-dimensional π phase grating is used, the following expression (11) is obtained from the expressions (9) and (10) on the basis of the expression (1).

$$Wx_i = \lambda/8Nd \times A_i \quad (11)$$

Likewise, in the case where the one-dimensional π/2 phase grating is used, the following expression (12) is obtained.

$$Wx_i = \lambda/4Nd \times A_i \quad (12)$$

The above-described calculation is performed for the overall pixels in the light reception region of the X-ray intensity detector 70, whereby the calculator 80 calculates the differential wavefront Wx of the transmitted wavefront 13 with a high degree of accuracy even if an uneven distribution is included in the transmissivity of the object 20 to be detected.

At one edge (right edge in FIG. 1) on the X-ray intensity detector 70, a region A to which the X-ray which does not pass through the object 20 to be detected is radiated is provided.

Since the X-ray wavefront in the region A is not influenced by the object 20 to be detected, the transmitted wavefront 13 is obtained by integrating the differential wavefront Wx from the region A toward the other edge (x direction in FIG. 1).

Since the shape of the transmitted wavefront indicates a path length in the path through which the X-ray of the object 20 to be detected is transmitted, a spatial change of a refractive index in the object 20 to be detected can be known by measuring the transmitted wavefront 13, and further an aspect of a spatial change of the composition can be known based on the spatial change of the refractive index.

Incidentally, the object 20 to be detected is disposed above the first grating 30 (+ side on the z axis in FIG. 1) in this example. However, even if the object to be detected is disposed immediately below the first grating, the differential wavefront Wx can be obtained in the same method as that described above.

Example 2

An example 2 will be described with reference to FIGS. 2A, 2B, 3A, 3B, 4A and 4B.

The first grating in this example is a phase modulation grating of a phase difference π which is two-dimensionally and periodically arranged (hereinafter, called a two-dimensional π phase grating).

Therefore, also the second grating has a two-dimensional periodic structure. Since the constituent elements other than the first grating and the second grating are the same as those in the example 1, these elements respectively have the same corresponding numerals as those illustrated in FIG. 1.

Figure 2A:
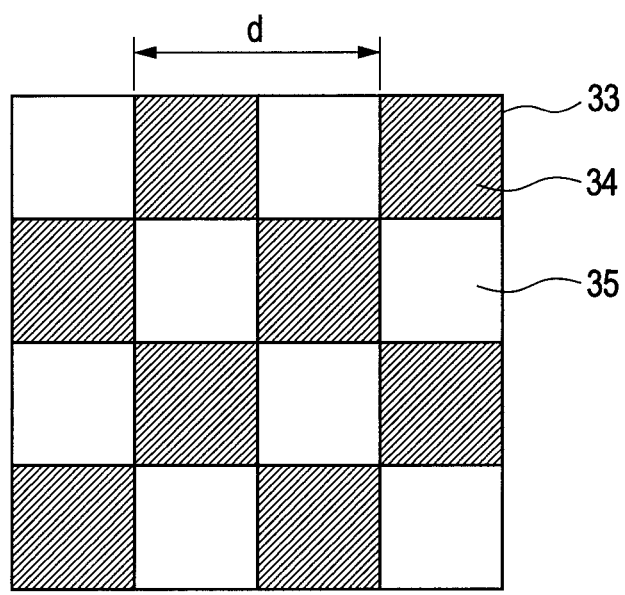
[FIGS. 2A and 2B]

FIG. 2A is the diagram which is obtained by viewing a part of the first grating in this example from the side of the X-ray source. In the drawing, a first grating 33 includes portions 34 and 35 of which the transmission phases are mutually different by π and which are periodically arranged checkerwise.

The distance $Z_0$ between the X-ray source and the first grating and the distance $Z_1$ between the first grating and the second grating satisfy the above expression (1)

Here, d indicates the grating period of the first grating illustrated in FIG. 2A, n indicates a natural number, and N indicates a real number which is expressed as n/4−⅛.

Figure 2B:
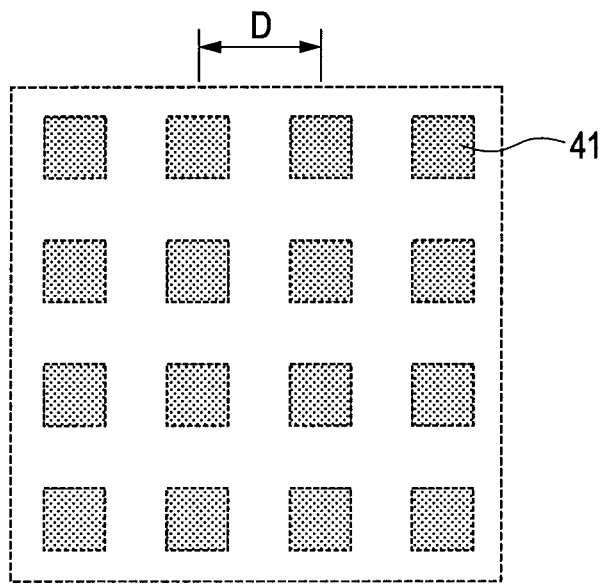

FIG. 2B is a diagram illustrating the bright-dark pattern which is generated on the second grating by the Talbot effect, and the bright-dark pattern has bright sections 41. The period D of the bright-dark pattern is expressed by the above expression (6) as well as the example 1.

The distance $Z_0$ between the X-ray source and the first grating, the distance $Z_1$ between the first grating and the second grating, and the grating period d are selected so that the period D is equivalent to 1/integer number of a pixel period p of the X-ray intensity detector 70.

Figure 3A:
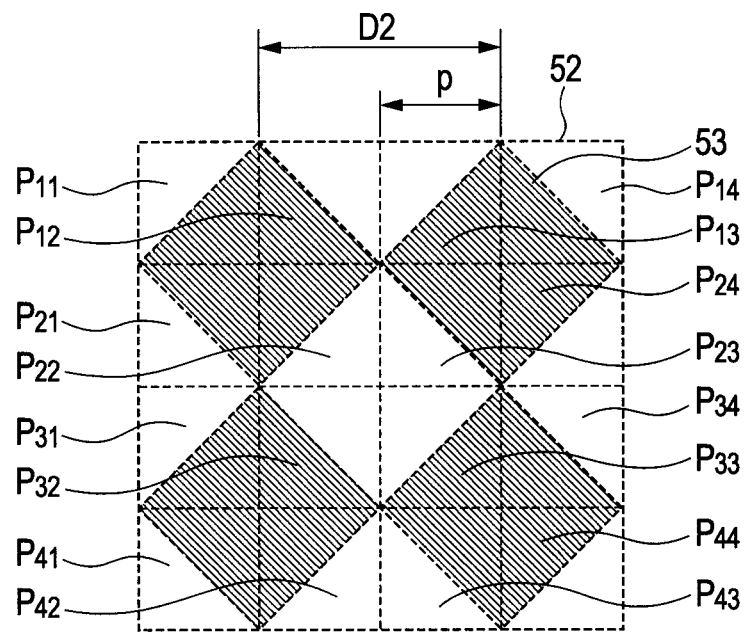
[FIGS. 3A and 3B]

FIG. 3A illustrates the structure of the second grating which is applied in a case where the period D is equivalent to the pixel period p of the X-ray intensity detector 70, and a positional relation between the blocking section of the second grating and the pixel of the X-ray intensity detector 70.

More specifically, respective portions $P_{ij}$ (i, j=1, 2, 3, . . . ) correspond to the pixels of the X-ray intensity detector 70, in which the borders of the pixels are indicated by the dotted lines, and a portion 52 corresponds to the second grating. A hatched portion 53 corresponds to the blocking section of the second grating 52, and a non-hatched portion corresponds to the light transmitting section. The blocking sections and the light transmitting sections are periodically arranged like 45°-inclined checkers. A period D2 of the second grating in the pixel arrangement direction is twice the pixel period p.

The direction in which the blocking section of the second grating 52 blocks a bright section 41 is set to be identical on the same pixel, the directions in which the blocking sections respectively block the bright sections on the adjacent pixels are set to be perpendicular to each other, and the directions in which the blocking sections respectively block the bright sections on the oblique pixels are set to be opposite to each other.

That is, the first blocking pattern of the first region on the pixel $P_{2i-1,2j-1}$ blocks the lower right half. Further, the second blocking pattern of the second region on the pixel $P_{2i,2j}$ blocks the upper left half. Furthermore, the third blocking pattern of the third region on the pixel $P_{2i-1,2j}$ blocks the lower left half. Furthermore, the fourth blocking pattern of the fourth region on the pixel $P_{2i,2j-1}$ blocks the upper right half.

Figure 3B:
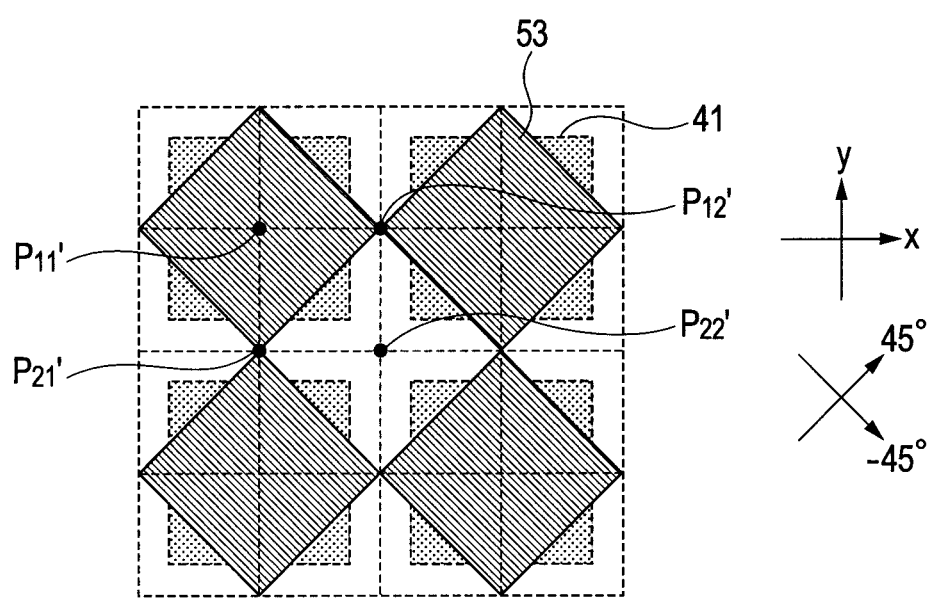

FIG. 3B is a diagram illustrating an overlapping state of the bright section 41 of the bright-dark pattern and the blocking section 53.

Here, the direction in which the blocking section 53 blocks the bright section 41 is the lower right of the pixel $P_{11}$, the lower left of the pixel $P_{12}$, the upper right of the pixel $P_{21}$, and the upper left of the pixel $P_{22}$. Hereinafter, the bright sections are likewise blocked every two pixel periods.

In the above state, if the bright section moves in the x direction due to an inclination of the wavefront, the amount of received light increases in each of the pixels $P_{12}$ and $P_{22}$, and the amount of received light decreases in each of the pixels $P_{11}$ and $P_{21}$. On the other hand, if the bright section moves in the y direction, the amount of received light increases in each of the pixels $P_{11}$ and $P_{12}$, and the amount of received light decreases in each of the pixels $P_{21}$ and $P_{22}$. Here, the x and y directions coincide with arrangement directions of pixels 61 (this is the same also in the following). Further, since the size of each pixel is generally small, the magnitude of intensity of the bright section 41 in one pixel can be considered to be approximately the same as that in its adjacent pixel, and also the magnitude of movement of the bright section 41 in one pixel can be considered to be approximately the same as that in its adjacent pixel. Therefore, a normalized intensity change which is obtained by dividing a difference between the outputs of the adjacent pixels by a sum of these outputs does not depend on the intensity of the bright sections 41, but is proportional only to an average value of the amounts of movements of the bright sections 41 of these four pixels.

That is, the normalized intensity changes $A_{11}$ and $B_{11}$ respectively concerning the movement components in the x and y directions at an intermediate position $P_{11}'$ of the pixels $P_{11}, P_{12}, P_{21}$ and $P_{22}$ are respectively defined by the following expressions (13) and (14).

Further, the normalized intensity changes $A_{21}$ and $B_{21}$ respectively concerning the movement components in the x and y directions at an intermediate position $P_{21}'$ of the pixels $P_{21}, P_{22}, P_{31}$ and $P_{32}$ are respectively defined by the following expressions (15) and (16).

In general, if the normalized intensity changes $A_{ij}$ and $B_{ij}$ respectively concerning the movement components in the x and y directions at an intermediate position of the pixels $P_{i,j}$, $P_{i,j+1}, P_{i+1,j}$ and $P_{i+1,j+1}$ are respectively defined by the following expressions (17) and (18), the normalized intensity changes $A_{ij}$ and $B_{ij}$ (i, j=1, 2, 3, . . . ) are proportional only to the changes of the bright section 41 in the x and y directions without being influenced by the transmissivity distribution of the object 20 to be detected.

$$A_{11}=(I_{12}+I_{22}-I_{11}-I_{21})/(I_{12}+I_{22}+I_{11}+I_{21}) \quad (13)$$

$$B_{11}=(I_{11}+I_{12}-I_{21}-I_{22})/(I_{11}+I_{12}+I_{21}+I_{22}) \quad (14)$$

$$A_{21}=(I_{22}+I_{32}-I_{21}-I_{31})/(I_{22}+I_{32}+I_{21}+I_{31}) \quad (15)$$

$$B_{21}=(I_{32}+I_{31}-I_{21}-I_{22})/(I_{32}+I_{31}+I_{21}+I_{22}) \quad (16)$$

$$A_{ij}=(-1)^j \times (I_{i,j}+I_{i+1,j}-I_{i,j+1}-I_{i+1,j+1})/(I_{i,j}+I_{i+1,j}+I_{i,j+1}+I_{i+1,j+1}) \quad (17)$$

$$B_{ij}=(-1)^i \times (I_{i+1,j}+I_{i+1,j+1}-I_{i,j}-I_{i,j+1})/(I_{i+1,j}+I_{i+1,j+1}+I_{i,j}+I_{i,j+1}) \quad (18)$$

The inclination $Wx_{ij}$ of the wavefront in the x direction is obtained from the following expression (19), in the same manner as that for obtaining $Wx_i$ by the expression (11) in the example 1.

$$Wx_{ij}=\lambda/4Nd \times A_{ij} \quad (19)$$

Likewise, the inclination $Wy_{ij}$ of the wavefront in the y direction is obtained from the following expression (20).

$$Wy_{ij}=\lambda/4Nd \times B_{ij} \quad (20)$$

Since the inclinations of the wavefront in the x and y directions are obtained as described above, the transmitted wavefront of the object 20 to be detected can be obtained by integrating the obtained inclinations.

In this example, since the inclination can be integrated in both the x and y directions, the transmitted wavefront of the object 20 to be detected can accurately be calculated even if there is no region which is provided on one edge of the X-ray intensity detector and to which the X-ray not passing through the object 20 to be detected is radiated.

Although the transmitted wavefront of the object 20 to be detected is calculated based on the movement components in the x and y directions of the bright section 41 in this example, the transmitted wavefront can also be calculated based on the movement components in 45° and −45° directions.

If the bright section 41 moves in the 45° direction in FIG. 3B, the amount of received light increases in the pixel $P_{12}$, the amount of received light decreases in the pixel $P_{21}$, and the amount of received light do not change in each of the pixels $P_{11}$ and $P_{22}$. On the other hand, if the bright section 41 moves in the −45° direction, the amount of received light increases in the pixel $P_{22}$, the amount of received light decreases in the pixel $P_{11}$, and the amount of received light do not change in each of the pixels $P_{12}$ and $P_{21}$. Even in this case, the following normalized intensity change is introduced.

That is, the normalized intensity changes $A_{11}$ and $B_{11}$ respectively concerning the movement components in the 45° and −45° directions at the intermediate position $P_{11}'$ of the pixels $P_{11}, P_{12}, P_{21}$ and $P_{22}$ are respectively defined by the following expressions (21) and (22).

Further, the normalized intensity changes $A_{21}$ and $B_{21}$ respectively concerning the movement components in the 45° and −45° directions at the intermediate position $P_{21}'$ of the pixels $P_{21}, P_{22}, P_{31}$ and $P_{32}$ are respectively defined by the following expressions (23) and (24).

In general, if the normalized intensity changes $A_{ij}$ and $B_{ij}$ respectively concerning the movement components in the 45° and −45° directions at the intermediate position $P_{i,j}'$ of the pixels $P_{i,j}, P_{i,j+1}, P_{i+1,j}$ and $P_{i+1,j+1}$ are respectively defined by the following expressions (25) and (26), the normalized intensity changes $A_{ij}$ and $B_{ij}$ (i, j=1, 2, 3, . . . ) are proportional only to the changes of the bright section 41 in the 45° and −45° directions without being influenced by the transmissivity distribution of the object 20 to be detected.

$$A_{11}=(I_{12}-I_{21})/(I_{12}+I_{21}) \quad (21)$$

$$B_{11}=(I_{22}-I_{11})/(I_{22}+I_{11}) \quad (22)$$

$$A_{21}=(I_{32}-I_{21})/(I_{32}+I_{21}) \quad (23)$$

$$B_{21}=(I_{22}-I_{31})/(I_{22}+I_{31}) \quad (24)$$

$$A_{ij}=(-1)^j \times (I_{i,j}-I_{i+1,j+1})/(I_{i,j}+I_{i+1,j+1}) \quad (i+j: \text{even number})$$

$$A_{ij}=(-1)^j \times (I_{i+1,j}-I_{i,j+1})/(I_{i+1,j}+I_{i,j+1}) \quad (i+j: \text{ odd number}) \quad (25)$$

$$B_{ij}=(-1)^j \times (I_{i+1,j}-I_{i,j+1})/(I_{i+1,j}+I_{i,j+1}) \quad (i+j: \text{ even number})$$

$$B_{ij}=(-1)^j \times (I_{i+1,j}-I_{i,j+1})/(I_{i+1,j}-I_{i,j+1}) \quad (i+j: \text{ odd number}) \quad (26)$$

The inclination $Wa_{ij}$ of the wavefront in the 45° direction is obtained from the following expression (27), in the same manner as that for obtaining $Wx_i$ by the expression (11) in the example 1.

$$Wa_{ij}=\lambda/4Nd \times A_{ij} \quad (27)$$

Likewise, the inclination $Wb_{ij}$ of the wavefront in the −45° direction is obtained from the following expression (28).

$$Wb_{ij}=\lambda/4Nd \times B_{ij} \quad (28)$$

Since the inclinations of the wavefront in the 45° and −45° directions are obtained as described above, the transmitted wavefront of the object 20 to be detected can be obtained by integrating the obtained inclinations.

As just described, the case where the period D of the bright-dark pattern is equivalent to the pixel period p of the X-ray intensity detector 70 is explained. The wavefront inclinations $Wx_{ij}$ and $Wy_{ij}$ can be likewise obtained even in a case where the period D is equivalent to 1/integer number of the pixel period p.

To decrease the period D implies to decrease the grading period d of the first grating. Hence, since the distance $Z_0$ between the X-ray source and the first grating and the distance $Z_1$ between the first grating and the second grating can be made small according to the above expression (1), the overall apparatus can be made compact in size.

Figure 4A:
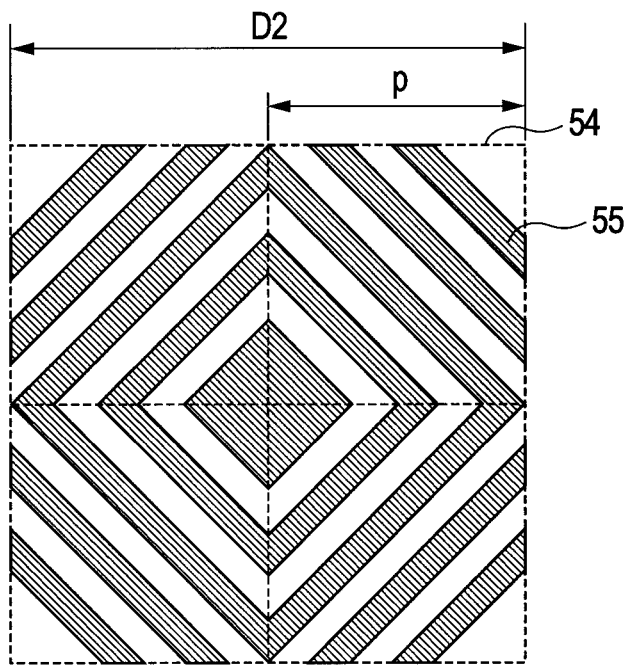
[FIGS. 4A and 4B]

FIG. 4A illustrates the structure of the second grating which is suitable in a case where the period D is ⅓ of the pixel period p of the X-ray intensity detector 70, and a positional relation between the blocking section of the second grating and the pixel of the X-ray intensity detector 70.

More specifically, a portion 54 corresponds to the second grating, a hatched portion 55 corresponds to the blocking section of the second grating, and the dotted lines indicate the borders of the pixels.

Figure 4B:
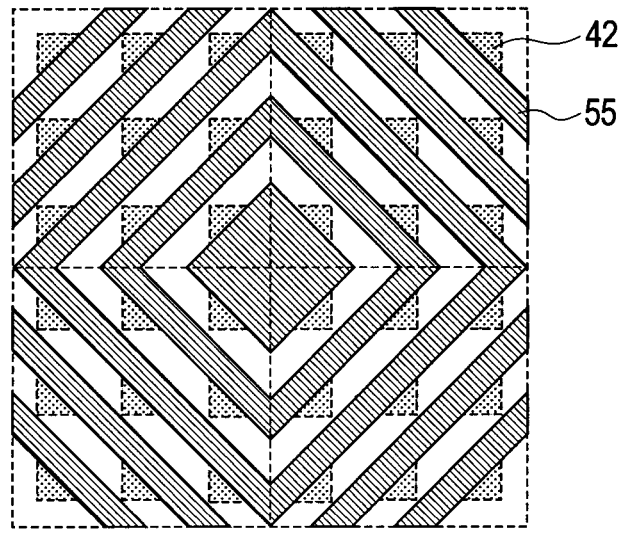

FIG. 4B illustrates an overlapping state of a bright section 42 of the bright-dark pattern and the blocking section 55. Here, the directions in which the blocking sections 55 respectively block the bright sections 42 are set to be the same on the same pixel, the directions in which the blocking sections 55 respectively block the bright sections 42 on the adjacent pixels are set to be perpendicular to each other, and the directions in which the blocking sections 55 respectively block the bright sections 42 on the oblique pixels are set to be opposite to each other. Namely, the above overlapping state is the same as that illustrated in FIG. 3B in the example 2. Therefore, the wavefront inclinations $Wx_{ij}$ and $Wy_{ij}$ can be calculated by using the expressions (17) to (20) or the expressions (25) to (28).

Example 3

An example 3 will be described with reference to FIGS. 5A, 5B, 6A and 6B.

Here, the blocking direction of the second grating in this example is different from that in the example 2, but other constituent elements are the same as those in the example 2.

Figure 5A:
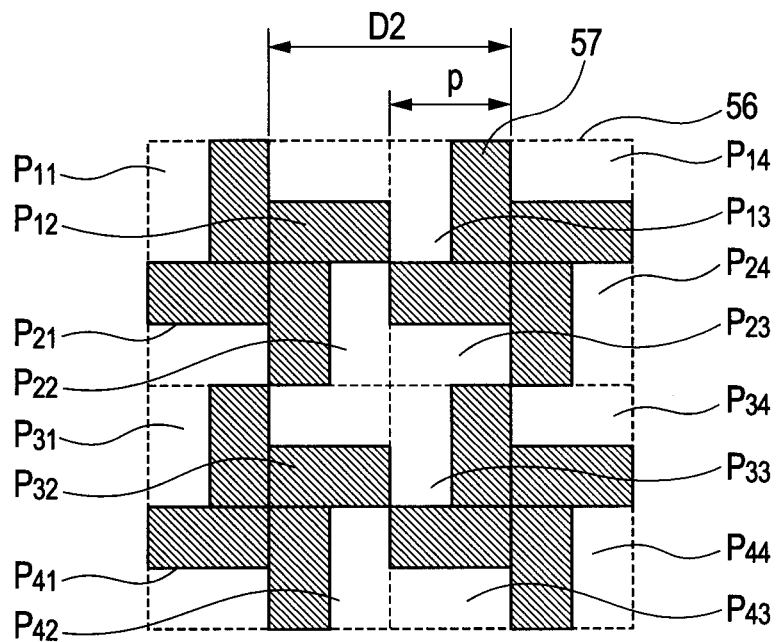
[FIGS. 5A and 5B]

FIG. 5A illustrates the structure of the second grating which is applied in a case where the period D is equivalent to the pixel period p of the X-ray intensity detector 70, and a positional relation between the blocking section of the second grating and the pixel of the X-ray intensity detector 70.

Here, respective portions $P_{ij}$ (i, j=1, 2, 3, . . . ) correspond to the pixels of the X-ray intensity detector 70, in which the borders of the pixels are indicated by the dotted lines, and a portion 56 corresponds to the second grating.

A hatched portion 57 corresponds to the blocking section of the second grating 56, and a non-hatched portion corresponds to the light transmitting section. The blocking sections and the light transmitting sections are periodically arranged so as to alternately block the upper, lower, left and right halves of the pixels. The period D2 of the second grating 56 in the pixel arrangement direction is twice the pixel period p. As well as the example 2, the direction in which the blocking section of the second grating 56 blocks the bright section is set to be identical on the same pixel, the directions in which the blocking sections respectively block the bright sections on the adjacent pixels are set to be perpendicular to each other, and the directions in which the blocking sections respectively block the bright sections on the oblique pixels are set to be opposite to each other.

That is, the first blocking pattern of the first region on the pixel $P_{2i-1,2j-1}$ blocks the right half. Further, the second blocking pattern of the second region on the pixel $P_{2i,2j}$ blocks the left half. Furthermore, the third blocking pattern of the third region on the pixel $P_{2i-1,2j}$ blocks the lower half. Furthermore, the fourth blocking pattern of the fourth region on the pixel $P_{2i,2j-1}$ blocks the upper half.

Figure 5B:
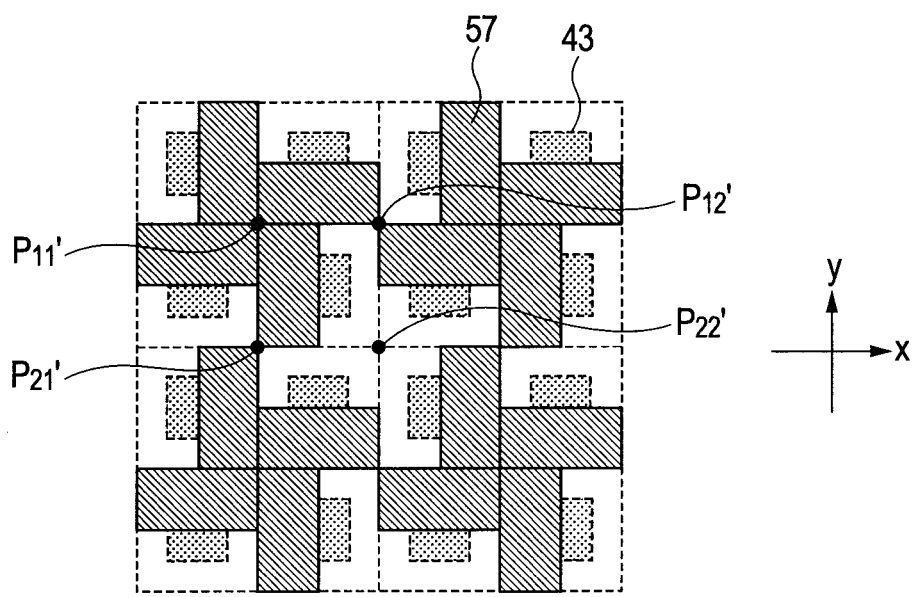

FIG. 5B illustrates an overlapping state of the bright section 43 of the bright-dark pattern and the blocking section 57.

Here, the blocking direction in this example is different from those of the second gratings 52 and 54 in the example 2. Namely, the direction in which the blocking section blocks the bright section is the right part of the pixel $P_{11}$, the lower part of the pixel $P_{12}$, the upper part of the pixel $P_{21}$, and the left part of the pixel $P_{22}$. Hereinafter, the bright sections are likewise blocked every two pixel periods.

In the above state, if the bright section 43 moves in the x direction due to an inclination of the wavefront, the amount of received light increases in the pixel $P_{22}$, the amount of received light decreases in the pixel $P_{11}$, and the amount of received light does not change in each of the pixels $P_{22}$ and $P_{21}$. On the other hand, if the bright section moves in the y direction, the amount of received light increases in the pixel $P_{12}$, the amount of received light decreases in the pixel $P_{21}$, and the amount of received light does not change in each of the pixels $P_{11}$ and $P_{22}$.

As well as the example 2, the normalized intensity change is introduced.

That is, the normalized intensity changes $A_{11}$ and $B_{11}$ respectively concerning the movement components in the x and y directions at the intermediate position $P_{11}'$ of the pixels $P_{11}$, $P_{12}$, $P_{21}$ and $P_{22}$ are respectively defined by the following expressions (29) and (30).

Further, the normalized intensity changes $A_{21}$ and $B_{21}$ respectively concerning the movement components in the x and y directions at the intermediate position $P_{21}'$ of the pixels $P_{21}$, $P_{22}$, $P_{31}$ and $P_{32}$ are respectively defined by the following expressions (31) and (32).

In general, if the normalized intensity changes $A_{ij}$ and $B_{ij}$ respectively concerning the movement components in the x and y directions at the intermediate position $P_{i,j}'$ of the pixels $P_{i,j}$, $P_{i,j+1}$, $P_{i+1,j}$ and $P_{i+1,j+1}$ are respectively defined by the following expressions (33) and (34), the normalized intensity changes $A_{ij}$ and $B_{ij}$ (i, j=1, 2, 3, . . . ) are proportional only to the changes of the bright section 43 in the x and y directions without being influenced by the transmissivity distribution of the object 20 to be detected.

$$A_{11}=(I_{22}-I_{11})/(I_{22}+I_{11}) \quad (29)$$

$$B_{11}=(I_{12}-I_{21})/(I_{12}+I_{21}) \quad (30)$$

$$A_{21}=(I_{22}-I_{31})/(I_{22}+I_{31}) \quad (31)$$

$$B_{21}=(I_{32}-I_{21})/(I_{32}+I_{21}) \quad (32)$$

$$A_{ij}=(-1)^i \times (I_{i,j}-I_{i+1,j+1})/(I_{i,j}+I_{i+1,j+1}) \ (i+j: \text{even number})$$

$$A_{ij}=(-1)^i \times (I_{i,j+1}-I_{i+1,j})/(I_{i+1,j}+I_{i,j+1}) \ (i+j: \text{odd number}) \quad (33)$$

$$B_{ij}=(-1)^j \times (I_{i+1,j}-I_{i,j+1})/(I_{i+1,j}+I_{i,j+1}) \ (i+j: \text{even number})$$

$$B_{ij}=(-1)^j \times (I_{i,j}-I_{i+1,j+1})/(I_{i,j}+I_{i+1,j+1}) \ (i+j: \text{odd number}) \quad (34)$$

After then, the inclinations of the wavefront in the x and y directions are obtained from the expressions (19) and (20) as well as the example 2, whereby the transmitted wavefront of the object 20 to be detected can be obtained by integrating the obtained inclinations.

As just described, the case where the period D of the bright-dark pattern is equivalent to the pixel period p of the X-ray intensity detector 70 is explained. The wavefront inclinations $Wx_{ij}$ and $Wy_{ij}$ can be likewise obtained even in the case where the period D is equivalent to 1/integer number of the pixel period p.

Figure 6A:
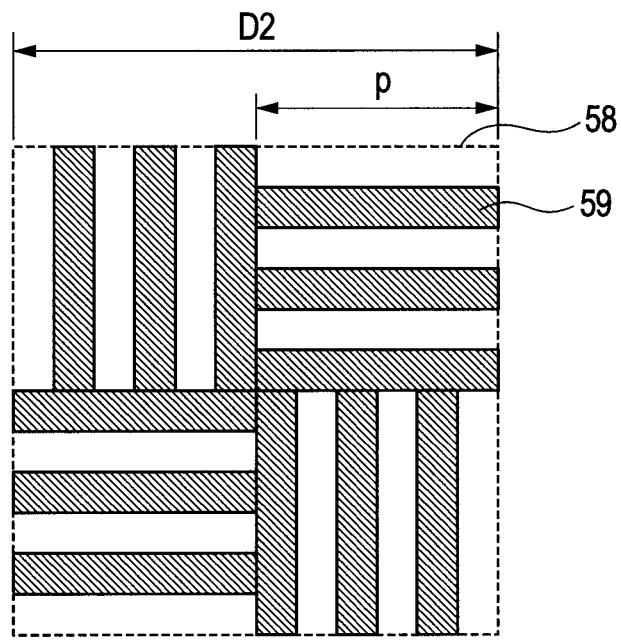
[FIGS. 6A and 6B]

FIG. 6A illustrates the structure of the second grating which is applied in a case where the period D is ⅓ of the pixel period p of the X-ray intensity detector 70, and a positional relation between the blocking section of the second grating and the pixel of the X-ray intensity detector 70. Here, a portion 58 corresponds to the second grating, a hatched portion 59 corresponds to the blocking section of the second grating, and the dotted lines indicate the borders of the pixels.

Figure 6B:
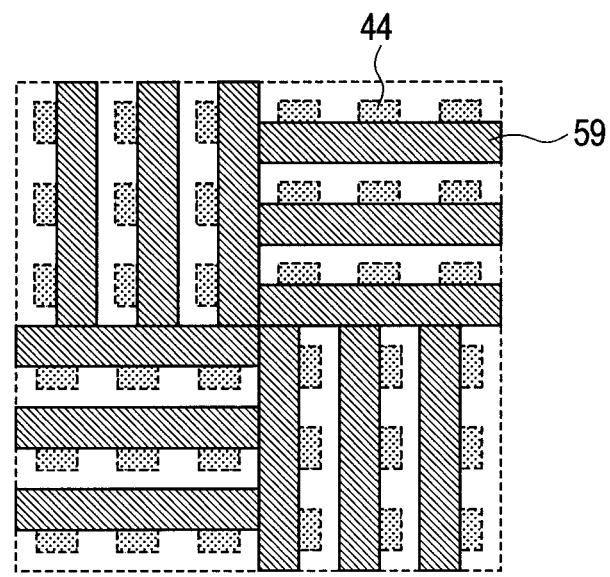

FIG. 6B illustrates an overlapping state of the bright section 44 of the bright-dark pattern and the blocking section 59.

Here, the direction in which the blocking section 59 blocks the bright section 44 is set to be identical on the same pixel, the directions in which the blocking sections respectively block the bright sections on the adjacent pixels are set to be perpendicular to each other, and the directions in which the blocking sections respectively block the bright sections on the oblique pixels are set to be opposite to each other. Namely, the overlapping state is the same as that illustrated in FIG. 5B.

Therefore, the wavefront inclinations $Wx_{ij}$ and $Wy_{ij}$ can be calculated by using the expressions (33), (34), (19) and (20).

Example 4

An example 4 will be described with reference to FIGS. 7A, 7B, 8A, 8B, 9A and 9B.

Here, the first grating in this example is a phase modulation grating of a phase difference π/2 which is two-dimensionally and periodically arranged (hereinafter, called a two-dimensional π/2 phase grating).

Therefore, also the second grating has a two-dimensional periodic structure of which the pattern is different from that in each of the examples 2 and 3.

Since the constituent elements other than the first grating and the second grating are the same as those in the example 1, these elements respectively have the same corresponding numerals as those illustrated in FIG. 1.

Figure 7A:
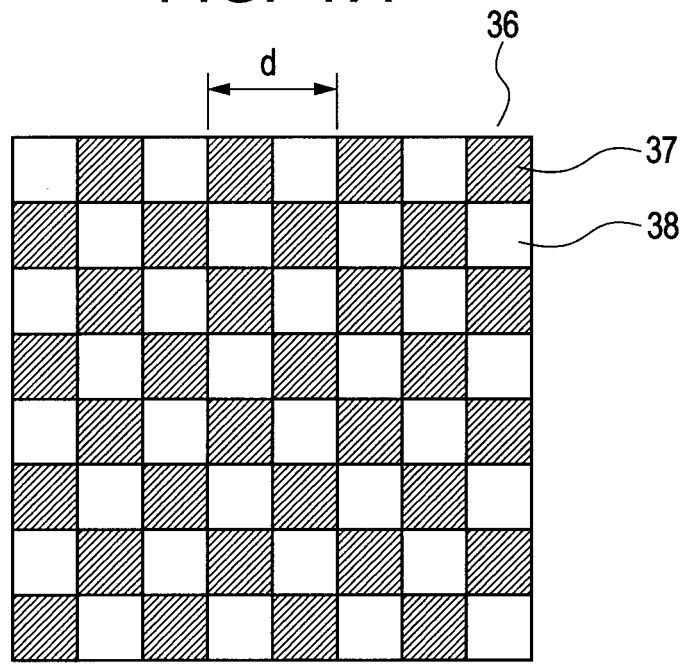
[FIGS. 7A and 7B]

FIG. 7A is the diagram which is obtained by viewing a part of the first grating in this example from the side of the X-ray source. In the drawing, a first grating 36 includes portions 37 and 38 of which the transmission phases are mutually different by π/2 and which are periodically arranged checkerwise.

The distance $Z_0$ between the X-ray source and the first grating and the distance $Z_1$ between the first grating and the second grating satisfy the above expression (1). In this case, d indicates the grating period of the first grating illustrated in FIG. 7A, n indicates a natural number, and N indicates a real number which is expressed as n/2−¼.

Figure 7B:
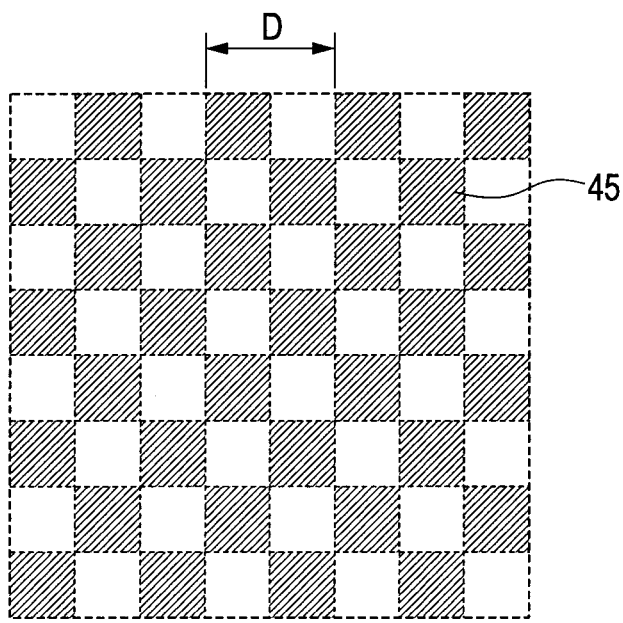

FIG. 7B illustrates the bright-dark pattern which is generated on the second grating by the Talbot effect, and the bright-dark pattern has a bright section/bright sections 45.

The period D of the bright-dark pattern is expressed by the expression (7) as well as the example 1. The distance $Z_0$ between the X-ray source and the first grating, the distance $Z_1$ between the first grating and the second grating, and the grating period d are selected so that the period D is equivalent to 1/integer number of the pixel period p of the X-ray intensity detector 70.

Figure 8A:
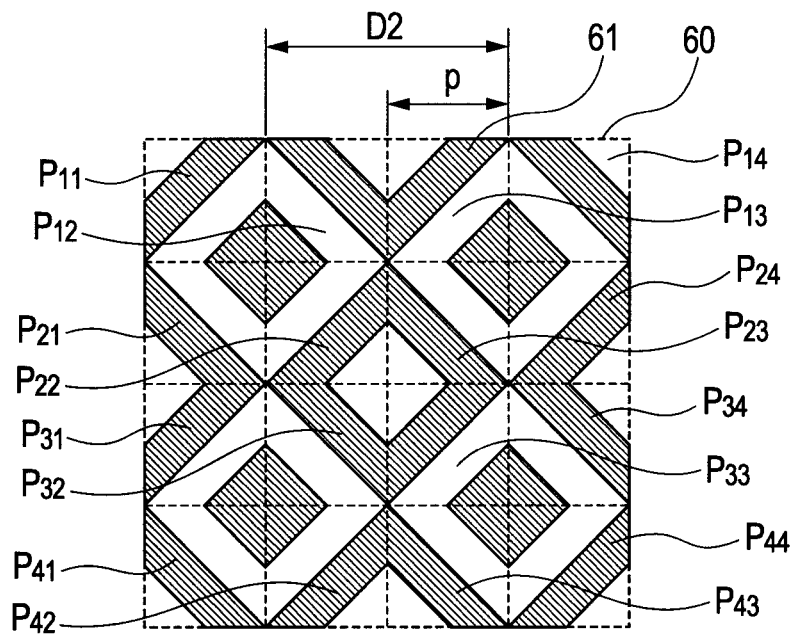
[FIGS. 8A and 8B]

FIG. 8A illustrates the structure of the second grating which is applied in the case where the period D is equivalent to the pixel period p of the X-ray intensity detector 70, and a positional relation between the blocking section of the second grating and the pixel of the X-ray intensity detector 70.

Here, respective portions $P_{ij}$ (i, j=1, 2, 3, . . . ) correspond to the pixels of the X-ray intensity detector 70, and the borders of the pixels are indicated by the dotted lines, and a portion 60 corresponds to the second grating. A hatched portion 61 corresponds to the blocking section of the second grating 60, and a non-hatched portion corresponds to the light transmitting section. The blocking sections and the light transmitting sections are two-dimensionally and periodically arranged. The period D2 of the second grating 60 in the pixel arrangement direction is twice the pixel period p. As well as the example 2, the direction in which the blocking section of the second grating 60 blocks the bright section is set to be identical on the same pixel, the directions in which the blocking sections respectively block the bright sections on the adjacent pixels are set to be perpendicular to each other, and the directions in which the blocking sections respectively block the bright sections on the oblique pixels are set to be opposite to each other.

That is, the first blocking pattern of the first region on the pixel $P_{2i-1,2j-1}$ blocks the upper left half. Further, the second blocking pattern of the second region on the pixel $P_{2i,2j}$ blocks the lower right half. Furthermore, the third blocking pattern of the third region on the pixel $P_{2i-1,2j}$ blocks the lower left half. Furthermore, the fourth blocking pattern of the fourth region on the pixel $P_{2i,2j-1}$ blocks the upper right half.

Figure 8B:
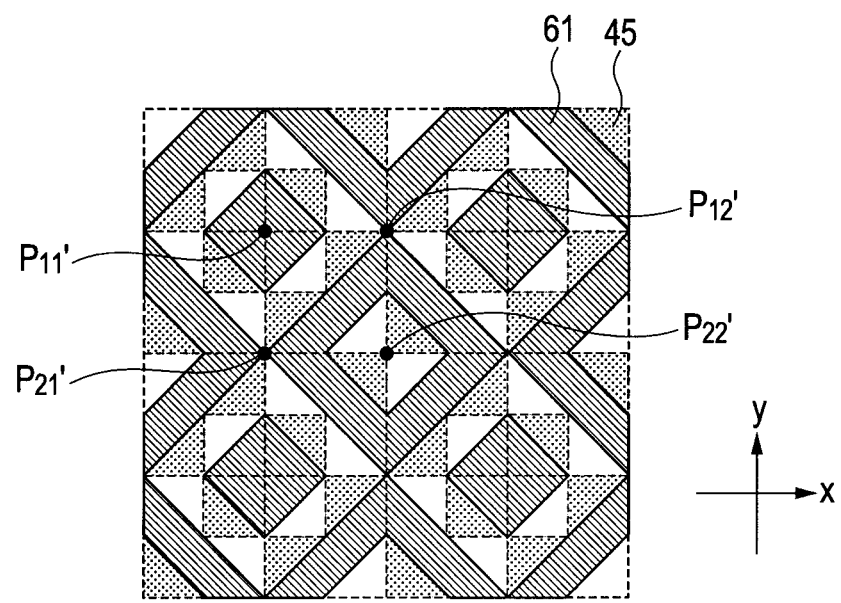

FIG. 8B illustrates an overlapping state of the bright section 45 of the bright-dark pattern and the blocking section 61.

Here, the direction in which the blocking section 61 blocks the bright section 43 is the upper left part of the pixel $P_{11}$, the lower left part of the pixel $P_{12}$, the upper right part of the pixel $P_{21}$, and the lower right part of the pixel $P_{22}$. Hereinafter, the bright sections are likewise blocked every two pixel periods.

In the above state, if the bright section 45 moves in the x direction due to an inclination of the wavefront, the amount of received light increases in each of the pixels $P_{11}$ and $P_{12}$, and the amount of received light decreases in each of the pixels $P_{21}$ and $P_{22}$. On the other hand, if the bright section moves in the y direction, the amount of received light increases in each of the pixels $P_{12}$ and $P_{22}$, and the amount of received light decreases in each of the pixels $P_{11}$ and $P_{21}$. As well as the example 2, the normalized intensity change is introduced.

That is, the normalized intensity changes $A_{11}$ and $B_{11}$ respectively concerning the movement components in the x and y directions at the intermediate position $P_{11}'$ of the pixels $P_{11}$, $P_{12}$, $P_{21}$ and $P_{22}$ are respectively defined by the following expressions (35) and (36).

Further, the normalized intensity changes $A_{21}$ and $B_{21}$ respectively concerning the movement components in the x and y directions at the intermediate position $P_{21}'$ of the pixels $P_{21}, P_{22}, P_{31}$ and $P_{32}$ are respectively defined by the following expressions (37) and (38).

In general, if the normalized intensity changes $A_{ij}$ and $B_{ij}$ respectively concerning the movement components in the x and y directions at the intermediate position $P_{i,j}'$ of the pixels $P_{i,j}, P_{i,j+1}, P_{i+1,j}$ and $P_{i+1,j+1}$ are respectively defined by the following expressions (39) and (40), the normalized intensity changes $A_{ij}$ and $B_{ij}$ (i, j=1, 2, 3, . . . ) are proportional only to the changes of the bright section 41 in the x and y directions without being influenced by the transmissivity distribution of the object 20 to be detected.

$$A_{11}=(I_{11}+I_{12}-I_{21}-I_{22})/(I_{11}+I_{12}+I_{21}+I_{22}) \quad (35)$$

$$B_{11}=(I_{12}+I_{22}-I_{11}-I_{21})/(I_{12}+I_{22}+I_{11}+I_{21}) \quad (36)$$

$$A_{21}=(I_{31}+I_{32}-I_{21}-I_{22})/(I_{31}+I_{32}+I_{21}+I_{22}) \quad (37)$$

$$B_{21}=(I_{22}+I_{32}-I_{21}-I_{31})/(I_{22}+I_{32}+I_{21}+I_{31}) \quad (38)$$

$$A_{ij}=(-1)^i \times (I_{i+1,j}+I_{i+1,j+1}-I_{i,j}-I_{i,j+1})/(I_{i+1,j}+I_{i+1,j+1}-I_{i,j}-I_{i,j+1}) \quad (39)$$

$$B_{ij}=(-1)^j \times (I_{i,j}+I_{i+1,j}-I_{i,j+1}-I_{i+1,j+1})/(I_{i,j}+I_{i+1,j}-I_{i,j+1}-I_{i+1,j+1}) \quad (40)$$

The inclination $Wx_{ij}$ of the wavefront in the x direction is obtained from the following expression (41), in the same manner as that for obtaining $Wx_i$ by the expression (12) in the example 1.

$$Wx_{ij}=\lambda/2Nd \times A_{ij} \quad (41)$$

Likewise, the inclination $Wy_{ij}$ of the wavefront in the y direction is obtained from the following expression (42).

$$Wy_{ij}=\lambda/2Nd \times B_{ij} \quad (42)$$

Since the inclinations of the wavefront in the x and y directions are obtained as described above, the transmitted wavefront of the object to be detected can be obtained by integrating the obtained inclinations.

Although the transmitted wavefront of the object 20 to be detected is calculated based on the movement components in the x and y directions of the bright section 45, it is apparent that the transmitted wavefront can also be calculated based on the movement components in 45° and −45° directions as well as the example 2. Therefore, the detail of such calculation will be omitted.

As just described, the case where the period D of the bright-dark pattern is equivalent to the pixel period p of the X-ray intensity detector 70 is explained. The wavefront inclinations $Wx_{ij}$ and $Wy_{ij}$ can be likewise obtained even in a case where the period D is equivalent to 1/integer number of the pixel period p.

Figure 9A:
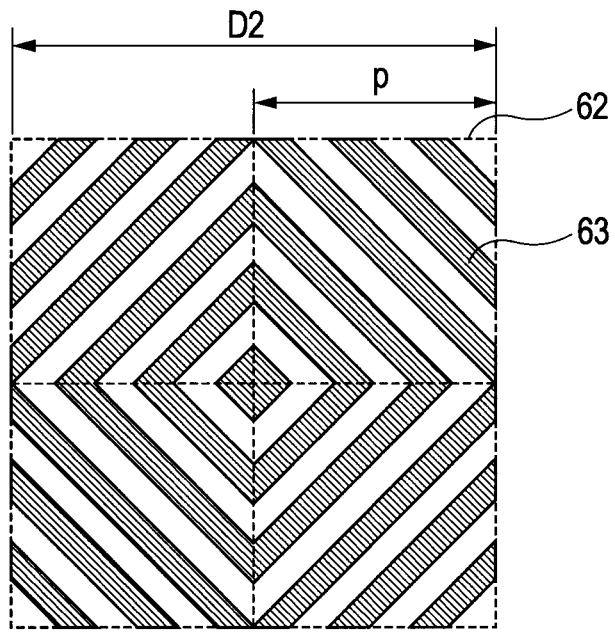
[FIGS. 9A and 9B]

FIG. 9A illustrates the structure of the second grating which is applied in a case where the period D is ⅓ of the pixel period p of the X-ray intensity detector 70, and a positional relation between the blocking section of the second grating and the pixel of the X-ray intensity detector 70.

Here, a portion 62 corresponds to the second grating, a hatched portion 63 corresponds to the blocking section, and the dotted lines indicate the borders of the pixels.

Figure 9B:
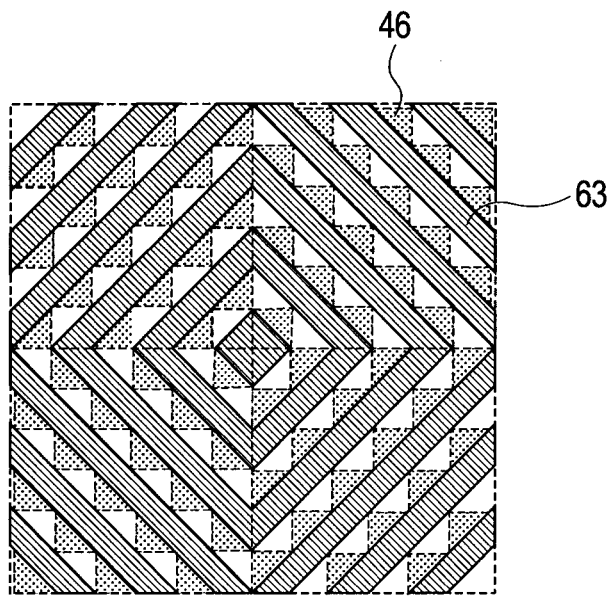

FIG. 9B illustrates an overlapping state of a bright section 46 of the bright-dark pattern and the blocking section 63.

Here, the directions in which the blocking sections 63 respectively block the bright sections 46 are set to be the same on the same pixel, the directions in which the blocking sections 63 respectively block the bright sections 46 on the adjacent pixels are set to be perpendicular to each other, and the directions in which the blocking sections 63 respectively block the bright sections 46 on the oblique pixels are set to be opposite to each other. Namely, the above overlapping state is the same as that illustrated in FIG. 3B in the example 2.

Therefore, the wavefront inclinations $Wx_{ij}$ and $Wy_{ij}$ can be calculated by using the expressions (39) to (42).

Example 5

An example 5 will be described with reference to FIGS. 10A and 10B.

Here, the first grating in this example is a two-dimensional amplitude grating of which the transmitting section is two-dimensionally and periodically arranged.

Figure 10A:
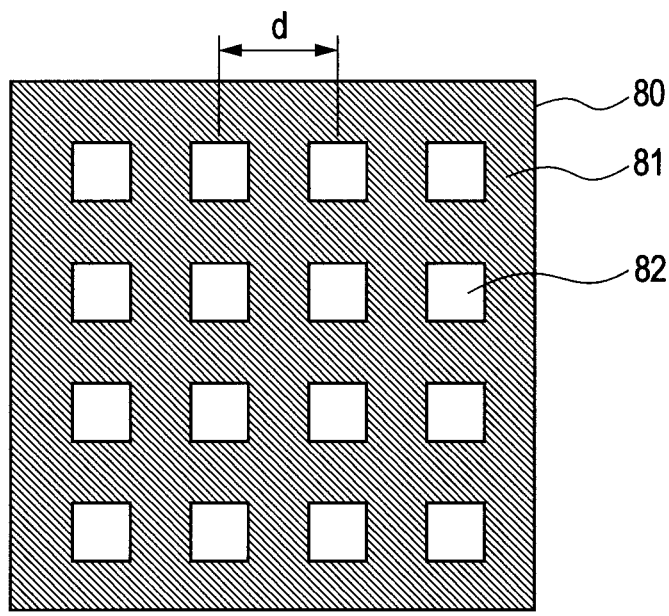
[FIGS. 10A and 10B]

FIG. 10A is the diagram which is obtained by viewing a part of the first grating from the side of the X-ray source.

In the drawing, a first grating 80 includes an absorption section 81 through which an X-ray does not transmit, and transmitting sections 82 through which X-rays transmit and are two-dimensionally arranged with periods d.

If the distance $Z_1$ between the first grating and the second grating is made small so that N in the expression (1) has a value sufficiently smaller than 1, the X-ray which transmitted through the transmitting section 82 approximately goes straight, thereby generating the bright-dark pattern on the second grating.

Figure 10B:
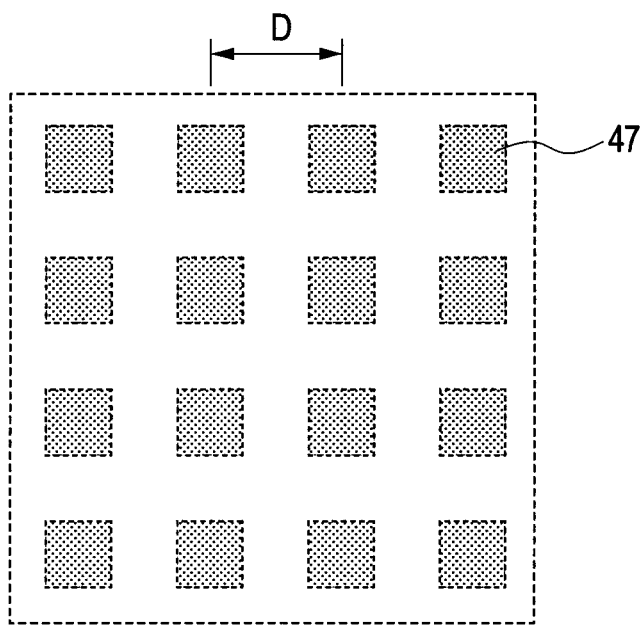

FIG. 10B illustrates the bright-dark pattern which is generated on the second grating, and includes bright sections 47.

The bright-dark pattern is similar to the arrangement pattern of the transmitting sections 82 of the first grating 80, and the period D thereof is expressed by the following expression (43).

In the expression, each of the distance $Z_0$ between the X-ray source and the first grating, the distance $Z_1$ between the first grating and the second grating, and the grating period d is selected to become 1/integer number of the pixel period p of the X-ray intensity detector 70.

$$D=(1+Z_1/Z_0) \times d \quad (43)$$

The second grating has the periodic-pattern blocking section. Thus, as well as the above examples, the blocking section blocks the bright sections 47 in the same direction in the pixel of the arranged X-ray intensity detector 70, and in the different directions respectively in the adjacent pixels.

In this example, since the bright-dark pattern is the same as those in the examples 2 and 3, the second grating has the pattern of the second grating illustrated in FIG. 3A, 4A, 5A or 6A according to a ratio of the period D of the bright-dark pattern and the pixel period, or the pattern which is similar to the above pattern.

Although a calculation expression of the transmitted wavefront of the object 20 to be detected depends on the pattern of the second grating, it will be easily led with reference to the calculation expressions as described in the above examples.

Industrial Applicability

As described above, according to the present invention, even if there is the non-uniformly distributed absorption in the object to be detected, it is possible to reduce the influence of the transmissivity distribution of the X-ray in the object to be detected, and it is thus possible to achieve the X-ray imaging apparatus capable of taking the phase image having exceptional quality.

While the present invention has been described with reference to the exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-036909, filed Feb. 23, 2010, which is hereby incorporated by reference herein in its entirety.

The invention claimed is:

1. An X-ray imaging apparatus which takes an image of an object to be detected, comprising:
a first grating configured to form a periodic bright-dark pattern by a Talbot effect, on the basis of an X-ray from an X-ray source;
a second grating, disposed at a position where the bright-dark pattern is formed, configured to block a part of the bright-dark pattern;
a detector configured to detect an X-ray intensity distribution of the X-ray which passed through the second grating; and
a calculator configured to calculate phase information of the X-ray on the basis of the X-ray intensity distribution detected by the detector,
wherein the second grating includes a first region in which a first blocking pattern has been formed and a second region in which a second blocking pattern has been formed,
wherein a direction in which the first blocking pattern blocks a bright section of the bright-dark pattern and a direction in which the second blocking pattern blocks the bright section of the bright-dark pattern are different from each other,
wherein the calculator calculates the phase information by obtaining a ratio of a sum of X-ray intensity information of the X-ray which passed through the first region and was detected in a pixel $P_i$ of the detector and X-ray intensity information of the X-ray which passed through the second region and was detected in a pixel $P_{i+1}$ of the detector to a difference between the X-ray intensity information of the X-ray which passed through the first region and was detected in the pixel $P_i$ of the detector and the X-ray intensity information of the X-ray which passed through the second region and was detected by the pixel $P_{i+1}$ of the detector, and then multiplying the obtained ratio by a proportionality constant, and
wherein i is an integer equal to or greater than one.

2. The X-ray imaging apparatus according to claim 1, wherein the direction in which the first blocking pattern blocks the bright section of the bright-dark pattern and the direction in which the second blocking pattern blocks the bright section of the bright-dark pattern are opposite to each other.

3. The X-ray imaging apparatus according to claim 2, wherein the second grating includes a third region in which a third blocking pattern for blocking the bright section of the bright-dark pattern in a direction perpendicular to the direction in which the first blocking pattern blocks the bright section of the bright-dark pattern has been formed, and a fourth region in which a fourth blocking pattern for blocking the bright section of the bright-dark pattern in a direction opposite to the direction in which the third blocking pattern blocks the bright section of the bright-dark pattern has been formed, and
the first region, the second region, the third region and the fourth region are adjacent to others.

4. An X-ray imaging system comprising:
the X-ray imaging apparatus described in claim 1; and
an X-ray source configured to irradiate the first grating with the X-ray.

5. The X-ray imaging apparatus according to claim 1, wherein the proportionality constant is determined by a distance between the first and second gratings, and a period of the first grating.

6. The X-ray imaging apparatus according to claim 1, wherein the proportionality constant is $D/4Z_1$, where D is a period of the bright-dark pattern, and $Z_1$ is a distance between the first and second gratings.

7. The X-ray imaging apparatus according to claim 1, wherein the proportionality constant is $\lambda/8d(n/4-1/8)$ when the first grating is a $\pi$ phase grating, and $\lambda/4d(n-1/2)$ when the first grating is a $\pi/2$ phase grating, where $\lambda$ is a wavelength of the X-ray, d is a grating period of the first grating, and n is a natural number.

8. The X-ray imaging apparatus according to claim 1, wherein the phase information is an average of the phase information in the pixel $P_i$ and the phase information in the pixel $P_{i+1}$.

9. The X-ray imaging apparatus according to claim 1, wherein the calculator obtains the phase information by using following expressions:

$$A_i = (-1)^i \times (I_{i+1} - I_i)/(I_{i+1} + I_i) = 4\Delta L_i/D; \text{ and}$$

$$Wx_i = \Delta L_i/Z_1,$$

where $I_i$ is an output of the pixel $P_i$, $I_{i+1}$ is an output of the pixel $P_{i+1}$, D is a period of the bright-dark pattern, $Z_1$ is a distance between the first and second gratings, and $Wx_i$ is an inclination of a wavefront in the x direction at the position corresponding to the pixel $P_i$, $A_i$ is a normalized intensity change obtained by dividing a difference between the outputs of the pixel $P_i$ and the pixel $P_{i+1}$ by a sum of these outputs, and $\Delta L_i$ is an average of the amount of the movements of the bright sections in the pixels P and $P_{i+1}$.

* * * * *